(12) United States Patent
Luo

(10) Patent No.: US 11,999,991 B2
(45) Date of Patent: Jun. 4, 2024

(54) OIL AND GAS EXPLORATION METHOD BASED ON MICROBIAL GENE

(71) Applicant: InSoil Energy Technology(Beijing)Co., Ltd., Beijing (CN)

(72) Inventor: Chuping Luo, Ezhou (CN)

(73) Assignee: INSOIL ENERGY TECHNOLOGY(BEIJING)CO.,LTD., Beijing (CN)

( * ) Notice: Subject to any disclaimer, the term of this patent is extended or adjusted under 35 U.S.C. 154(b) by 0 days.

(21) Appl. No.: 18/219,104

(22) Filed: Jul. 7, 2023

(65) Prior Publication Data

US 2024/0011072 A1 Jan. 11, 2024

(30) Foreign Application Priority Data

Jul. 8, 2022 (CN) .......................... 202210804571.5

(51) Int. Cl.
*C12Q 1/68* (2018.01)
*C12Q 1/64* (2006.01)
*C12Q 1/689* (2018.01)

(52) U.S. Cl.
CPC .............. *C12Q 1/64* (2013.01); *C12Q 1/689* (2013.01)

(58) Field of Classification Search
CPC .................... C12Q 1/64; C12Q 1/68
See application file for complete search history.

(56) References Cited

FOREIGN PATENT DOCUMENTS

| CN | 102174646 B | 3/2013 |
|---|---|---|
| CN | 104975067 B | 6/2018 |
| CN | 107267623 B | 6/2018 |
| CN | 106011241 B | 6/2020 |
| CN | 112301138 A | 2/2021 |
| CN | 112322697 A | 2/2021 |
| CN | 112760318 A | 5/2021 |

OTHER PUBLICATIONS

English translation of CN112301138A, Wang Qinghua et al. pub Feb. 2, 2021 (Year: 2021).*
English translation of CN107267623A, Luo Chuping et al. Oct. 20, 2017 (Year: 2017).*
English translation of CN112760318A, Zhang Jiabin et al. May 7, 2021 (Year: 2021).*
English translation of CN112322697A, Zhang Hudan et al. Feb. 5, 2021 (Year: 2021).*
English translation of CN106011241A, Deng Shicai et al. Oct. 12, 2016 (Year: 2016).*
Bucker et al., 2018. Evaluation of the deteriogenic microbial community using qPCR, n-alkanes and FAMEs biodegradation in diesel, biodiesel and blends (B5, B10, and B50) during storage. Fuel, 233, pp. 911-917. (Year: 2018).*
Chikere et al., 2021. Microbial communities in field-scale oil-polluted soil remediation using 16S rRNA amplicon sequencing. International Journal of Environmental Studies, 78(3), pp. 410-426. (Year: 2021).*
Deng et al., 2018. Novel butane-oxidizing bacteria and diversity of bmoX genes in Puguang gas field. Frontiers in Microbiology, 9, 1576, pp. 1-13. (Year: 2018).*
Dutra et al., 2023. Corrosion-influencing microorganisms in petroliferous regions on a global scale: systematic review, analysis, and scientific synthesis of 16S amplicon metagenomic studies. PeerJ, 11, p. e14642. (Year: 2023).*
Fan et al., 2017. Profiling of sulfate-reducing bacteria in an offshore oil reservoir using phospholipid fatty acid (PLFA) biomarkers. Water, Air, & Soil Pollution, 228, pp. 1-16. (Year: 2017).*
Fierer et al., 2007. Metagenomic and small-subunit rRNA analyses reveal the genetic diversity of bacteria, archaea, fungi, and viruses in soil. Applied and environmental microbiology, 73(21), pp. 7059-7066. (Year: 2007).*
Gomes et al., 2023. Metabolically Active Microbial Communities in Oilfields: A Systematic Review and Synthesis of RNA Preservation, Extraction, and Sequencing Methods. Applied Microbiology, 3(4), pp. 1144-1163. (Year: 2023).*
Kimes et al., 2013. Metagenomic analysis and metabolite profiling of deep-sea sediments from the Gulf of Mexico following the Deepwater Horizon oil spill. Frontiers in microbiology, 4, 50, pp. 1-17. (Year: 2013).*
Lenchi et al., 2013. Diversity of microbial communities in production and injection waters of Algerian oilfields revealed by 16S rRNA gene amplicon 454 pyrosequencing. PloS one, 8(6), e66588, pp. 1-14. (Year: 2013).*
Okpala et al., 2021. Molecular Methods for Assessing Microbial Corrosion and Souring Potential in Oilfield Operations. In Microbial Bioinformatics in the Oil and Gas Industry (pp. 169-205). CRC Press. (Year: 2021).*
Rachel, N.M. and Gieg, L.M., 2020. Preserving microbial community integrity in oilfield produced water. Frontiers in Microbiology, 11, 581387, pp. 1-10. (Year: 2020).*

(Continued)

*Primary Examiner* — Stephanie K Mummert
*Assistant Examiner* — Olayinka A Oyeyemi
(74) *Attorney, Agent, or Firm* — Bayramoglu Law Offices LLC

(57) ABSTRACT

An oil and gas exploration method based on a microbial gene is provided, where samples are collected from shallow surface layers above a known oil well, a gas well, and a dry well in an exploration area, DNA is extracted and subjected to high-throughput sequencing (HTS), and a pattern map of a microbial community composition in the exploration area is established according to sequencing results; and characteristic microorganisms in surface soil above an oil/gas well in the exploration area are screened out according to the pattern map, then primers are designed according to attribute characters of the characteristic microorganisms, and samples throughout the exploration area are subjected to fluorescence quantitative polymerase chain reaction (PCR) to detect a number of the characteristic microorganisms.

5 Claims, 2 Drawing Sheets

(56) References Cited

OTHER PUBLICATIONS

Radwan et al., 2018. Robust multiplex quantitative polymerase chain reaction assay for universal detection of microorganisms in fuel. Energy & Fuels, 32(10), pp. 10530-10539. (Year: 2018).*

Rajbongshi et al., 2021. A review on anaerobic microorganisms isolated from oil reservoirs. World Journal of Microbiology and Biotechnology, 37(7), 111, pp. 1-19. (Year: 2021).*

Song et al., 2017. Wellhead samples of high-temperature, low-permeability petroleum reservoirs reveal the microbial communities in wellbores. Energy & Fuels, 31(5), pp. 4866-4874. (Year: 2017).*

Wietz et al., 2022. Impact of preservation method and storage period on ribosomal metabarcoding of marine microbes: Implications for remote automated samplings. Frontiers in Microbiology, 13, p. 999925. (Year: 2022).*

Yasir et al., 2021. 16S amplicon sequencing of microbial communities in enriched and non-enriched sediments of non-volcanic hot spring with temperature gradients. PeerJ, 9, e10995, pp. 1-22. (Year: 2021).*

English translation of CN104975067A, Wang Jianghai et al. Oct. 14, 2015 (Year: 2015).*

English translation of CN102174646A, Wang Jianghai et al. Sep. 7, 2011 (Year: 2011).*

\* cited by examiner

OIL AND GAS EXPLORATION METHOD BASED ON MICROBIAL GENE

CROSS REFERENCE TO THE RELATED APPLICATIONS

This application is based upon and claims priority to Chinese Patent Application No. 202210804571.5, filed on Jul. 8, 2022, the entire contents of which are incorporated herein by reference.

TECHNICAL FIELD

The present disclosure belongs to the technical field of oil and gas exploration, and relates to an oil and gas exploration method based on a microbial gene.

BACKGROUND

Since 1955, the China General Microbiological Culture Collection Center (CGMCC), Chinese Academy of Sciences has cooperated with the Ministry of Petroleum Industry to carry out research on gaseous hydrocarbon-oxidizing bacteria and microbiological exploration methods in oil and gas fields. During the development for more than half a century, oil and gas microbial exploration technology has undergone a large number of field applications, with excellent application results. In terms of providing direct evidence of hydrocarbon enrichment, the oil and gas microbial exploration technology exhibits advantages that other technologies do not have, and has become a widely-recognized oil and gas exploration technology.

With the development of microbial detection technologies, a microbial exploration method with genetic testing as a technical means has shown promising application prospects. For example, in the patents (granted Chinese patent publication No.: CN 102174646 B and CN 104975067 B), a cultivation method and a fluorescence quantitative polymerase chain reaction (PCR) method are used to detect total bacterial count (TBC) abnormalities and viable bacterial count (VBC) abnormalities in methane-oxidizing bacteria or butane-oxidizing bacteria. Bacterial lines are plotted, and abnormalities in methane-oxidizing bacteria and abnormalities in butane-oxidizing bacteria are combined, and docked with geological, geochemical, and geophysical exploration results to evaluate and predict petroleum resources in an exploration area. The patent (granted Chinese patent publication No.: CN 106011241 B) provides a probe set, chip, kit, and exploration method for oil and gas exploration, where the probe set is designed according to a 16s rRNA gene and alkB, alkH, alkJ, alkK, pmoA, mmoX, and BmoX genes of microorganisms; it has excellent specificity and high accuracy, and is independent of cultivation. In the patent (granted Chinese patent publication No.: CN 107267623 B), a cultivation method is first used to detect a content of butane-oxidizing bacteria, an isopleth is plotted, and an abnormal area of butane-oxidizing bacteria is determined. Then, a number of lower hydrocarbon-oxidizing bacteria in the identified abnormal exploration area are detected by fluorescence quantitative PCR, and according to two results in combination with surface factors, a candidate well position is determined.

The disclosed microbial exploration technology based on genetic testing provides a large number of detection indexes and microbial genetic information related to hydrocarbon oxidation, and related evidence for oil and gas exploration can be obtained through various data processing and interpretation methods. However, the previous exploration technology with genetic testing as a means does not fully consider differences of microorganisms in different target exploration areas, and methods involved all are based on abnormal numbers of specific microorganisms to identify oil and gas enrichment, which lacks the extraction of microbial information for forward-modeling of well positions in a target area, and does not consider the differences of microbial species in different target exploration areas. If microbial information for forward-modeling well positions is not fully considered, some acquired data may be invalid data or interference data, resulting in an incorrect determination of an exploration area. The extraction of effective information from forward modeling and the extended application of extracted information to unknown areas is an effective means to improve the success rate of microbial exploration.

In addition, there are currently few studies on a preservation agent for soil samples, and there is no special preservation agent for preservation of soil samples including oil and gas microorganisms.

SUMMARY

In view of the above problems, the present disclosure provides an oil and gas exploration method based on a microbial gene. Samples are collected from shallow surface layers above a known oil/gas well and a dry well in an exploration area, DNA is extracted and subjected to high-throughput sequencing (HTS), and a pattern map of a microbial species composition in the exploration area is established according to sequencing results; and characteristic microorganisms in surface soil above an oil/gas well in the exploration area are screened out according to the pattern map, and then primers are designed according to attribute characters of the characteristic microorganisms to directly conduct fluorescence quantitative PCR. Preservation agents for soil samples are investigated and optimized, and a special preservation agent for preservation of a soil sample including oil and gas microorganisms is developed.

The present disclosure discloses an oil and gas exploration method based on a microbial gene, including the following steps:

S1. determining a sampling site in an exploration area;

S2. determining a sampling site in a forward-modeling area, where the sampling site in the forward-modeling area refers to a sampling site above a known well within or adjacent to the exploration area;

S3. designing a sampling scheme for the forward-modeling area, and collecting and preserving a sample;

S4. extracting DNA from the sample;

S5. subjecting the sample from the forward-modeling area to HTS, and reading operational taxonomic unit (OTU) values of species;

S6. establishing an oil and gas-indicating microbial fingerprint of the exploration area, and identifying gas-indicating effective bacteria and/or oil-indicating effective bacteria in the exploration area; and calculating oil indexes and/or gas indexes according to the OTU values, and comparing values of the oil indexes and/or the gas indexes to determine effective oil indexes and/or effective gas indexes;

S7. designing corresponding primers according to the gas-indicating effective bacteria and/or the oil-indicating effective bacteria identified based on the oil and gas-indicating microbial fingerprint, and conducting fluorescence quantitative PCR to obtain an oil-indicating microbial value and/or a gas-indicating microbial value of the sampling site; and S8. according to microbial results and geophysical and petroleum geological data, comprehensively determining an oil and gas area through a multi-disciplinary and multi-field technology.

In some embodiments of the present disclosure, the known well includes one or more selected from the group consisting of a dry well, a water well, a display well, and an industrial well.

In some embodiments of the present disclosure, the HTS refers to HTS of a 16S rDNA gene or a hydrocarbon oxidation-associated gene, and the hydrocarbon oxidation-associated gene includes one or more selected from the group consisting of a pmoA gene, a mmoX gene, a bmoX gene, an alk gene, and a P450 gene.

In some embodiments of the present disclosure, when the effective oil indexes and/or the effective gas indexes are determined, among the oil indexes, the first 5 species with a maximum oil/gas value greater than 2 are determined as the effective oil indexes; and among the gas indexes, the first 5 species with a maximum gas/oil value greater than 2 are determined as the effective gas indexes.

In some embodiments of the present disclosure, a sampling depth is 20 cm to 100 cm; and in some embodiments of the present disclosure, a sampling amount is 50 g to 100 g.

In some embodiments of the present disclosure, the sample is preserved at −20° C. or the sample is preserved with a preservation agent.

In some embodiments of the present disclosure, the preservation agent includes a DNase inhibitor, a metal ion chelating agent, and 3-mercaptoethanol, and can protect the DNA molecular integrity for a long time.

In some preferred embodiments of the present disclosure, the preservation agent further includes ascorbic acid and a derivative thereof.

In some preferred embodiments of the present disclosure, a concentration of the cetyltrimethylammonium bromide (CTAB) in the preservation agent is 1% (w/v) to 2% (w/v).

In some preferred embodiments of the present disclosure, a concentration of the ethanol in the preservation agent is 2% (v/v) to 4.5% (v/v).

In some preferred embodiments of the present disclosure, a concentration of the β-mercaptoethanol in the preservation agent is 1% (v/v) to 3% (v/v).

In some preferred embodiments of the present disclosure, a concentration of the ascorbic acid and the derivative thereof in the preservation agent is 0.5 mM to 1.5 mM.

In some preferred embodiments of the present disclosure, the ascorbic acid and the derivative thereof refer to a mixture of ascorbic acid and ascorbyl palmitate in a molar ratio of 3:1.

In some preferred embodiments of the present disclosure, a concentration of the ethylenediaminetetraacetic acid disodium salt in the preservation agent is 5 mM to 10 mM.

In some preferred embodiments of the present disclosure, a concentration of the DNase inhibitor in the preservation agent is 1 mg/L to 2 mg/L.

In some embodiments of the present disclosure, the preservation agent includes the following components:
CTAB: 0.5% (w/v) to 2% (w/v); ethanol: 2% (v/v) to 4.5% (v/v); 3-mercaptoethanol: 1% (v/v) to 3% (v/v); ascorbic acid: 0.5 mM to 1 mM; ascorbyl palmitate: 0.1 mM to 0.5 mM; ethylenediaminetetraacetic acid disodium salt: 5 mM to 10 mM; NaCl: 0.2 mM to 0.5 mM; DNase inhibitor: 1 mg/L to 2 mg/L; and pH 8.0 Tris-HCl: the balance.

In some embodiments of the present disclosure, during the sampling in S3, an optimal sampling depth of the sampling site is determined through the following steps:

S31. sampling at each of 10 cm, 20 cm, 30 cm, 40 cm, 50 cm, 60 cm, 70 cm, 80 cm, 90 cm, and 100 cm;

S32. detecting a total number of microorganisms at sampling depths of 50 cm and 60 cm;

S33. comparing total numbers of microorganisms at the two sampling depths;

S34. selecting a sampling depth nearest to one of the two sampling depths that has a larger total number of microorganisms than the other one, and detecting a total number of microorganisms at the sampling depth;

S35. repeating S33 and S34 until no sample is available for detection;

S36. calculating the optimal sampling depth as follows:

$$H_{opt}=\text{Log}^{-1}[Hm-a\Sigma(H-b)a/4(100-Hm-Hn)],$$

where Hm represents a logarithmic value of a sampling depth with a maximum total number of microorganisms, a represents a constant of 6 to 9, b represents a correction depth of cm to 60 cm, H represents a sampling depth at which a total number of microorganisms is detected, and Hn represents a logarithmic value of a sampling depth with a minimum total number of microorganisms.

The present disclosure has the following beneficial technical effects:

In the oil and gas exploration method based on a microbial gene in the present disclosure, HTS results of known well samples are used to determine effective oil and/or gas-indicating bacteria, and primers are designed accordingly; values of indicating microorganisms obtained can well predict an oil and gas distribution in an entire exploration area; effective indicating bacteria are screened to greatly reduce a size of data that need to be processed and reduce the data noise; and prediction results are superior to prediction results of the existing oil and gas microbial method.

An isopleth of oil and gas-indicating microorganism values obtained by the oil and gas exploration method based on a microbial gene in the present disclosure not only has a high coincidence rate with a known well, but also can have an excellent coincidence rate with a trap line and finely characterize an oil area.

DETAILED DESCRIPTION OF THE EMBODIMENTS

Figure 1:
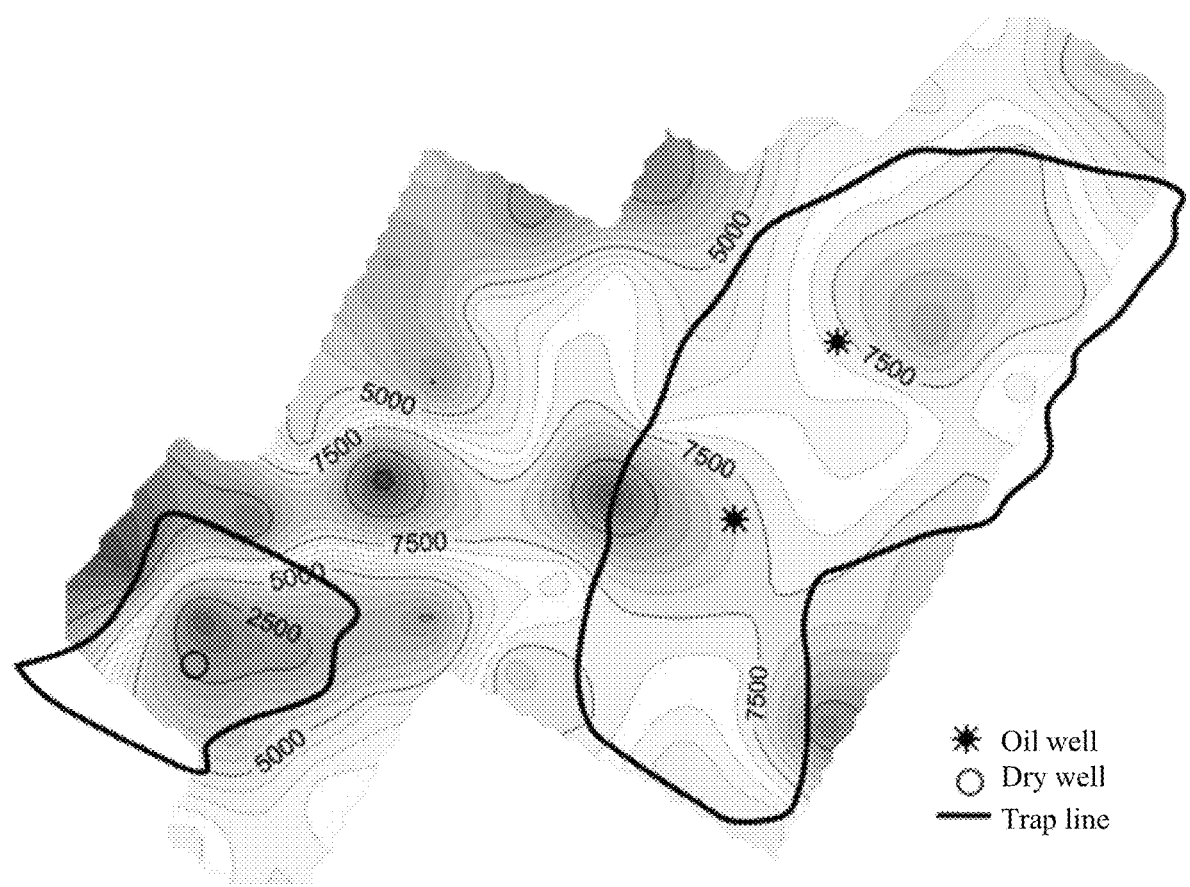
FIG. 1 shows an isopleth of oil and gas-indicating microbial values of a specified area obtained according to a patented method of the patent (granted patent publication No.: CN 107267623 B)

The embodiments of the present disclosure are described below through specific examples, and those skilled in the art can easily understand other advantages and effects of the present disclosure from the contents disclosed in this specification. The present disclosure can also be implemented or applied through other different specific implementations. Based on different viewpoints and applications, various modifications or alterations can be made to various details of this specification without departing from the spirit of the present disclosure.

Example 1

This example provided an oil and gas exploration method based on a microbial gene for oil and gas exploration in a specified exploration area, including the following steps:

Early sample collection was the same as the sample collection for oil and gas microbial exploration.

Specific steps were as follows:

1. Based on a geological background of an exploration area and preliminary research findings, a technical service scheme was customized in view of the problems and difficulties in the current exploration.

A. The scheme design is very flexible, and the design should consider an expected size and shape of an exploration target, whether sampling is allowed along or between key seismic survey lines, construction feasibility, and complexity of a surface environment.

B. According to different exploration targets, a spacing between sampling sites varies greatly, and can range from 50 m to 100 m to 500 m to 1,000 m.

C. A forward model must be established with a known well in an exploration area or an area adjacent to the exploration area as a target, and the known well preferably includes a dry well, a water well, a display well, and an industrial well.

2. According to the design scheme, a surveyor calculated coordinates of each site.

3. A sampling depth was determined according to surface characteristics and human activities of the exploration area. Studies of the present disclosure showed that the sampling depth was 20 cm to 60 cm.

4. A sampling amount was determined according to indexes to be detected. Studies of the present disclosure showed that the sampling amount was 50 g to 100 g.

5. A preservation manner of a sample was determined according to indexes to be detected. Studies of the present disclosure showed that a sample was preserved at −20° C.

6. DNA was extracted from each sample.

7. Samples from a forward-modeling area (a known oil/gas well) were subjected to HTS of a 16S rDNA gene or a hydrocarbon oxidation-associated gene. The hydrocarbon oxidation-associated gene included one or more selected from the group consisting of the identified pmoA gene, mmoX gene, bmoX gene, alk gene, and P450 gene.

OTU values of species were read. Data were shown in Table 1.

TABLE 1

HTS data

| No. | Species | Dry well | Oil well | Gas well |
|---|---|---|---|---|
| 1 | s_Acidobacteria_bacterium_WX27 | 11.00 | 20.00 | 21.00 |
| 2 | s_agricultural_soil_bacterium_SC-I-11 | 1.30 | 2.60 | 0.88 |
| 3 | s_agricultural_soil_bacterium_SC-I-39 | 1.00 | 7.00 | 14.60 |
| 4 | s_Bacillus_aryabhattai | 1.67 | 2.20 | 0.00 |
| 5 | s_bacterium_Ellin517 | 4.17 | 6.20 | 2.56 |
| 6 | s_bacterium_Ellin6537 | 2.33 | 2.60 | 6.78 |
| 7 | s_bacterium_Ellin6543 | 9.00 | 39.60 | 42.00 |
| 8 | s_bacterium_endosymbiont_of_Onthophagus_Taurus | 1.83 | 0.00 | 15.00 |
| 9 | s_bacterium_enrichment_culture_clone_auto10_4W | 1.00 | 8.00 | 5.11 |
| 10 | s_bacterium_enrichment_culture_clone_auto112_4W | 1.00 | 1.20 | 2.89 |
| 11 | s_bacterium_enrichment_culture_clone_auto195_4W | 4.17 | 2.00 | 4.22 |
| 12 | s_bacterium_enrichment_culture_clone_auto84_4W | 7.00 | 5.20 | 7.56 |
| 13 | s_bacterium_enrichment_culture_clone_B302011 | 4.83 | 3.60 | 16.33 |
| 14 | s_Candidatus_Yanofskybacteria_bacterium_GW2011_GWA2_41_22 | 3.00 | 3.00 | 4.00 |
| 15 | s_Catellatospora_sp._KC-EP-S6 | 2.17 | 0.20 | 39.44 |
| 16 | s_Cylindrotheca_closterium | 1.50 | 13.80 | 2.44 |
| 17 | s_delta_proteobacterium_WX81 | 2.17 | 1.80 | 7.78 |
| 18 | s_Gemmata_sp._F11-1 | 5.00 | 9.20 | 13.00 |
| 19 | s_Gemmatirosa_kalamazoonesis | 0.33 | 0.00 | 2.11 |
| 20 | s_groundwater_metagenome | 1.00 | 5.40 | 2.89 |
| 21 | s_marine_metagenome | 1.67 | 4.00 | 23.56 |
| 22 | s_Mesorhizobium_ciceri | 2.83 | 4.20 | 1.33 |
| 23 | s_Methylobacterium_radiotolerans | 0.33 | 1.60 | 0.67 |
| 24 | s_miscellaneous_Crenarchaeota_group_archaeon_SMTZ-80 | 4.67 | 39.40 | 2.11 |
| 25 | s_Oryza_longistaminata | 0.33 | 3.00 | 8.00 |
| 26 | s_Parcubacteria_group_bacterium_GW2011_GWA2_40_14 | 3.17 | 9.60 | 1.89 |
| 27 | s_Planctomycetaceae_bacterium_LX124 | 1.83 | 1.20 | 2.11 |
| 28 | s_Planctomycetaceae_bacterium_SCGC_AG-212-F19 | 2.33 | 2.40 | 0.67 |
| 29 | s_planctomycete_A-2 | 4.17 | 13.00 | 2.33 |
| 30 | s_planctomycete_WY69 | 6.17 | 6.40 | 17.44 |
| 31 | s_Planctomycetia_bacterium_WSF3-27 | 13.83 | 16.60 | 72.67 |
| 32 | s_Pythium_insidiosum | 0.00 | 0.60 | 0.78 |
| 33 | s_Rhodococcus_erythropolis | 1.00 | 1.20 | 1.11 |
| 34 | s_soil_bacterium_WF55 | 0.33 | 2.00 | 1.00 |
| 35 | s_soil_bacterium_WWH121 | 1.50 | 1.20 | 5.00 |
| 36 | s_Sphingomonas_paucimobilis | 1.17 | 3.00 | 5.00 |
| 37 | s_Spirochaeta_sp._MWH-HuW8 | 1.50 | 1.40 | 1.44 |
| 38 | s_Streptomyces_cinnamonensis | 5.00 | 5.20 | 3.44 |
| 39 | s_Turneriella_parva | 2.00 | 3.00 | 4.56 |
| 40 | s_wastewater_metagenome | 1.00 | 7.60 | 9.00 |
| 41 | s_Weissella_confusa | 0.83 | 1.20 | 12.78 |

Note:
The OTU value indicates an average OTU value of samples collected above a well.

8. An oil and gas-indicating microbial fingerprint of the exploration area was established, and gas-indicating effective bacteria and/or oil-indicating effective bacteria in the exploration area were identified.

Oil indexes and/or gas indexes were calculated according to OTU values.

(1) Oil index=OTU value in an oil well/OTU value in a dry well, and gas index=OTU value in a gas well/OTU value in a dry well. The first 10 with a maximum value were selected from each of the oil indexes and the gas indexes. Species corresponding to each of the oil indexes and the gas indexes were screened out. Results were shown in Tables 2 and 3.

TABLE 2

| | | | | | | | |
|---|---|---|---|---|---|---|---|
| | Oil indexes | | | | | | |
| No. | Species | Dry well | Oil well | Gas well | Oil index | Gas index | Gas/oil |
| 7 | s_bacterium_Ellin6543 | 9.00 | 39.60 | 42.00 | 4.40 | 4.67 | 0.94 |
| 23 | s_Methylobacterium_radiotolerans | 0.33 | 1.60 | 0.67 | 4.80 | 2.00 | 2.40* |
| 20 | s_groundwater_metagenome | 1.00 | 5.40 | 2.89 | 5.40 | 2.89 | 1.87 |
| 34 | s_soil_bacterium_WF55 | 0.33 | 2.00 | 1.00 | 6.00 | 3.00 | 2.00 |
| 3 | s_agricultural_soil_bacterium_SC-I-39 | 1.00 | 7.00 | 14.60 | 7.00 | 14.60 | 0.48 |
| 40 | s_wastewater_metagenome | 1.00 | 7.60 | 9.00 | 7.60 | 9.00 | 0.84 |
| 9 | s_bacterium_enrichment_culture_clone_auto10_4W | 1.00 | 8.00 | 5.11 | 8.00 | 5.11 | 1.57 |
| 24 | s_miscellaneous_Crenarchaeota_group_archaeon_SMTZ-80 | 4.67 | 39.40 | 2.11 | 8.44 | 0.45 | 18.66* |
| 25 | s_Oryza_longistaminata | 0.33 | 3.00 | 8.00 | 9.00 | 24.00 | 0.38 |
| 16 | s_Cylindrotheca_closterium | 1.50 | 13.80 | 2.44 | 9.20 | 1.63 | 5.65* |

*effective index

TABLE 3

| | | | | | | | |
|---|---|---|---|---|---|---|---|
| | Gas indexes | | | | | | |
| No. | Species | Dry well | Oil well | Gas well | Oil index | Gas index | Gas/oil |
| 9 | s_bacterium_enrichment_culture_clone_auto10_4W | 1.00 | 8.00 | 5.11 | 8.00 | 5.11 | 0.64 |
| 31 | s_Planctomycetia_bacterium_WSF3-27 | 13.83 | 16.60 | 72.67 | 1.20 | 5.25 | 4.38* |
| 19 | s_Gemmatirosa_kalamazoonesis | 0.33 | 0.00 | 2.11 | 0.00 | 6.33 | — |
| 8 | s_bacterium_endosymbiont_of_Onthophagus_Taurus | 1.83 | 0.00 | 15.00 | 0.00 | 8.18 | — |
| 40 | s_wastewater_metagenome | 1.00 | 7.60 | 9.00 | 7.60 | 9.00 | 1.18 |
| 21 | s_marine_metagenome | 1.67 | 4.00 | 23.56 | 2.40 | 14.13 | 5.89* |
| 3 | s_agricultural_soil_bacterium_SC-I-39 | 1.00 | 7.00 | 14.60 | 7.00 | 14.60 | 2.09 |
| 41 | s_Weissella_confusa | 0.83 | 1.20 | 12.78 | 1.44 | 15.33 | 10.65* |
| 15 | s_Catellatospora_sp._KC-EP-S6 | 2.17 | 0.20 | 39.44 | 0.09 | 18.21 | 197.22* |
| 25 | s_Oryza_longistaminata | 0.33 | 3.00 | 8.00 | 9.00 | 24.00 | 2.67* |

*effective index (2) Then values of the oil indexes and gas indexes were compared. Among the oil indexes, the first 5 species with a maximum oil/gas value greater than 2 were determined as effective oil indexes; and among the gas indexes, the first 5 species with a maximum gas/oil value greater than 2 were determined as effective gas indexes.

In this embodiment, the determined oil indexes were s_Methylobacterium_radiotolerans(O-1), s_miscellaneous_Crenarchaeota_group_archaeon_SMTZ-80(O-2), and s_Cylindrotheca_closterium(O-3); and the determined effective gas indexes were s_Catellatospora_sp._KC-EP-S6(G-1), s_Weissella_confusa(G-2), s_marine_metagenome(G-3), s_Oryza_longistaminata(G-4), and s_Planctomycetia_bacterium_WSF3-27(G-5).

In actual oil and gas exploration, there is relatively low probability that both an oil well and a gas well exist in a same work area. If there is only an oil well or a gas well, there is no need to consider the results of oil/gas when oil indexes and gas indexes are screened.

In this embodiment, some invalid data were processed at an early stage of data processing, such that the later data processing was convenient and the later data processing results were intuitive.

The elimination of inefficient bacteria (with a relatively small proportion in each of the dry well, oil well, and gas well) during PCR detection could significantly reduce a reading when there was no oil and gas, namely, a background noise reading, which improved a signal-noise ratio (SNR) and improved the accuracy of exploration prediction.

9. Corresponding primers were designed according to the effective indexes identified based on the oil and gas-indicating microbial fingerprint, and fluorescence quantitative PCR was conducted to obtain an oil-indicating microbial value and/or a gas-indicating microbial value.

10. According to microbial results and geophysical and petroleum geological data, an oil and gas area was comprehensively determined through a multi-disciplinary and multi-field technology.

Figure 2:
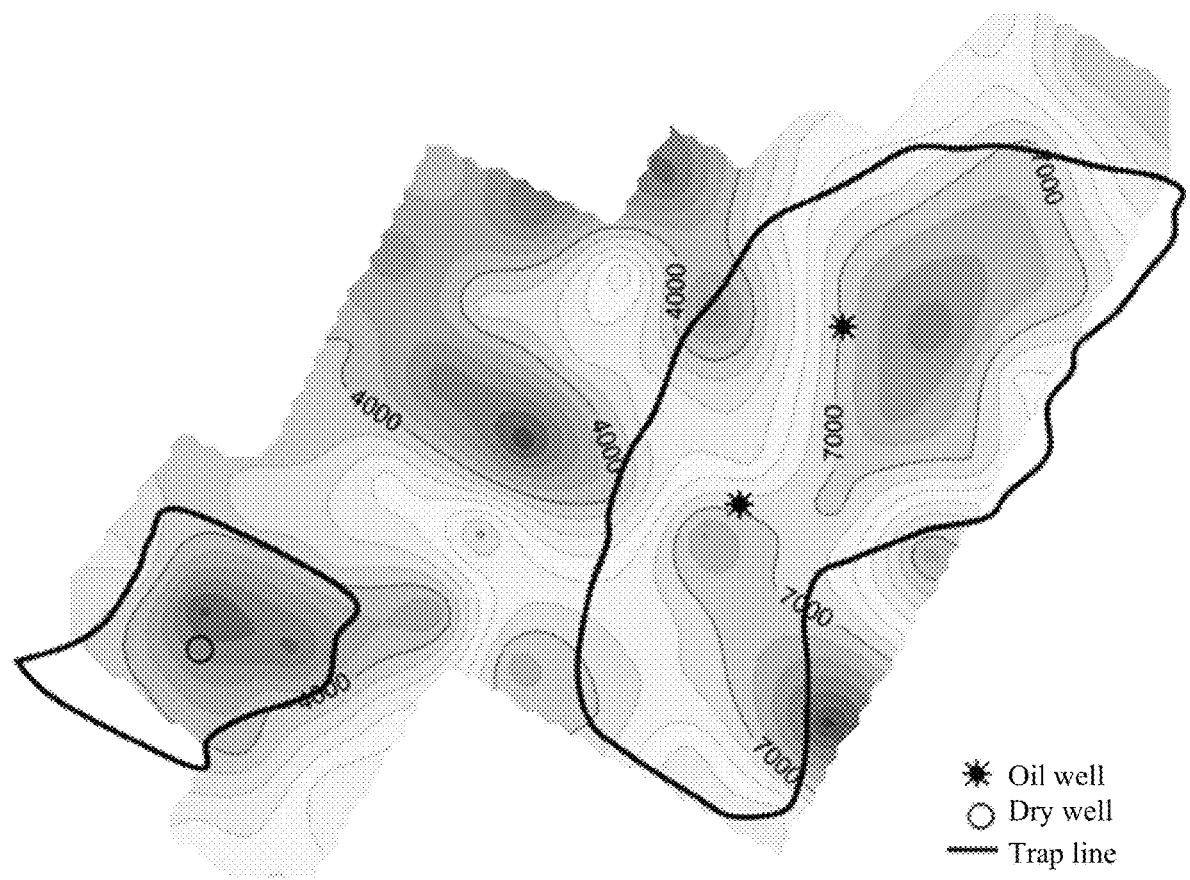
FIG. 2 shows an isopleth of oil and gas-indicating microbial values of the same area obtained according to an embodiment of the present disclosure.

FIG. 2 shows an isopleth of microbial values of the exploration area obtained according to the method in Example 1 of the present disclosure. FIG. 1 shows an isopleth of the same area obtained according to a method of the patent (granted patent publication No.: CN 107267623 B). It can be seen from FIG. 1 that although the isopleth has a high coincidence rate with a known well, it is not so obvious in the background area and abnormal area, and there are still many high points outside a trap, which may form a "pseudo-abnormal band" with other undefined abnormal points. It can be seen from FIG. 2 that the isopleth not only has a high coincidence rate with a known well, but also can have an excellent coincidence rate with a trap line and finely characterize an oil area.

Example 2 Research on a Preservation Effect of a Sample Preservation Agent

Formula 1 of the preservation agent:
CTAB: 0.5% (w/v); ethanol: 2% (v/v); β-mercaptoethanol: 1% (v/v); ascorbic acid: 0.9 mM; ascorbyl palmitate: 0.1 mM; ethylenediaminetetraacetic acid disodium salt: 10 mM; NaCl: 0.5 mM; DNase inhibitor: 1 mg/L; and pH 8.0 Tris-HCl: the balance.

Formula 2 of the preservation agent:
CTAB: 2% (w/v); ethanol: 4.5% (v/v); β-mercaptoethanol: 3% (v/v); ascorbic acid: 0.9 mM; ascorbyl palmitate: 0.1 mM; ethylenediaminetetraacetic acid disodium salt: 5 mM; NaCl: 0.2 mM; DNase inhibitor: 2 mg/L; and pH 8.0 Tris-HCl: the balance.

Formula 3 of the preservation agent:
CTAB: 1% (w/v); ethanol: 3% (v/v); β-mercaptoethanol: 2% (v/v); ascorbic acid: 0.9 mM; ascorbyl palmitate: 0.1 mM; ethylenediaminetetraacetic acid disodium salt: 8 mM; NaCl: 0.3 mM; DNase inhibitor: 2 mg/L; and pH 8.0 Tris-HCl: the balance.

Formula 4 of the preservation agent:
CTAB: 0.5% (w/v); ethanol: 2% (v/v); β-mercaptoethanol: 1% (v/v); ascorbic acid: 0.5 mM; ascorbyl palmitate: 0.5 mM; ethylenediaminetetraacetic acid disodium salt: 10 mM; NaCl: 0.5 mM; DNase inhibitor: 1 mg/L; and pH 8.0 Tris-HCl: the balance.

Formula 5 of the preservation agent:
CTAB: 0.5% (w/v); ethanol: 2% (v/v); β-mercaptoethanol: 1% (v/v); ascorbic acid: 0.75 mM; ascorbyl palmitate: 0.25 mM; ethylenediaminetetraacetic acid disodium salt: 10 mM; NaCl: 0.5 mM; DNase inhibitor: 1 mg/L; and pH 8.0 Tris-HCl: the balance.

Preparation method of the preservation agent:
According to the formula, the ethanol and β-mercaptoethanol were added to the Tris-HCl, a resulting mixture was thoroughly stirred, then the CTAB, ascorbyl palmitate, ascorbic acid, ethylenediaminetetraacetic acid disodium salt, NaCl, and DNase inhibitor were added, and a resulting mixture was stirred for dissolution.

The preparation of the preservation agent was conducted in a sterile environment, and the preservation agent was filtered through a 0.25 μm filter membrane to allow sterilization for later use.

The preservation agent of the above formula was added to a fresh sample obtained in Example 1 according to a volume ratio of 1:1, then a resulting mixture was preserved at 25° C. for 72 h, and total DNA was extracted according to a conventional method, which was an experimental group. Total DNA was extracted from a sample not preserved with the preservation agent of formula 1 (processing time: less than 4 h) and used as a control, which was recorded as 100%. Total DNA extraction rates obtained were shown in the table below:

| | Total DNA extraction rate/% |
|---|---|
| Preservation agent of formula 1 (preservation at 25° C. for 72 h) | 90.2b |
| Preservation agent of formula 2 (preservation at 25° C. for 72 h) | 91.3b |
| Preservation agent of formula 3 (preservation at 25° C. for 72 h) | 92.7b |
| Preservation agent of formula 4 (preservation at 25° C. for 72 h) | 92.3b |
| Preservation agent of formula 5 (preservation at 25° C. for 72 h) | 96.4a |
| Preservation agent of formula 1 (no preservation) | 100a |

The results show that a total DNA extraction rate of a sample preserved with the preservation agent of formulas 1 to 5 for 3 d at room temperature is greater than 90%, which can meet the requirements of the agent; and the preservation agent of formula 5 has the optimal performance.

The preferred specific implementations and examples of the present disclosure are described in detail above, but the present disclosure is not limited to the above implementations and examples. Within the knowledge of those skilled in the art, various variations can also be made without departing from the concept of the present disclosure.

What is claimed is:

1. An oil and gas exploration method based on a microbial gene, comprising the following steps:
    S1) determining a sampling site in an exploration area;
    S2) determining a sampling site in a forward-modeling area, wherein the forward-modeling area is established with a known oil containing well, and/or with a known gas containing well in the exploration area; or wherein the forward-modeling area is established with a known well within an area that is adjacent to the exploration area; wherein the sampling site of the forward-modeling area is above the known oil and/or gas containing well in the exploration area, or wherein the sampling site of the forward-modeling area is above the known well within an area adjacent to the exploration area;
    S3) designing a scheme for sampling the forward-modeling area, wherein the sampling scheme involves collecting and preserving a soil sample from one or more sampling sites above each well in the forward modeling area;
    wherein the soil samples include microorganisms and each collected soil sample is preserved with a preservation agent comprising of the following components:
    a Tris-HCl solution pH 8.0 comprising a 0.5% (w/v) cetyltrimethylammonium bromide (CTAB), a 2% (v/v) ethanol, a 1% (v/v) β-mercaptoethanol, 0.75 mM ascorbic acid, 0.25 mM ascorbyl palmitate, 10 mM ethylenediaminetetraacetic acid disodium salt, 0.5 mM NaCl, and 1 mg/L DNase inhibitor;
    S4) extracting DNA from the preserved soil samples of the one or more sampling sites in the forward modeling area;
    S5) subjecting the extracted DNA from each soil sample from the forward-modeling area to a high-throughput sequencing (HTS), and reading operational taxonomic unit (OTU) values of species at each sampling site; and
    S6) identifying gas-indicating effective bacteria and/or oil-indicating effective bacteria at each sampling site within the exploration area;
    calculating oil indexes and/or gas indexes according to the OTU values of the soil sample at each sampling site within the exploration area, and/or the OTU values of the gas-indicating effective bacteria in a known well that is a dry well and in a known well that is an oil well; and/or the OTU values of the oil-indicating effective bacteria in a known well that is a dry well and in a known well that is an oil well;
    comparing the values of the oil indexes and/or the gas indexes to determine effective oil indexes and/or effective gas indexes at each sampling site within the exploration area; and
    establishing an isopleth of oil and gas-indicating microorganism values at each sampling site across the exploration area using the values of the effective oil indexes and/or effective gas indexes at each sampling site.

2. The method according to claim 1, wherein the known well is a dry well, a water well, a display well, or an industrial well.

3. The method according to claim 1, wherein the HIS is a HIS of a 16S rDNA gene or a hydrocarbon oxidation-associated gene, and the hydrocarbon oxidation-associated gene comprises one or more selected from the group consisting of a pmoA gene, an mmoX gene, a bmoX gene, an alk gene, and a P450 gene.

4. The method according to claim 1, wherein the effective oil indexes are selected for the first 5 species with a maximum oil/gas value greater than 2 and wherein the effective gas indexes are selected for the first 5 species with a maximum gas/oil value greater than 2.

5. The method according to claim 1, wherein the soil sample is collected at a sampling depth that is from 20 cm to 100 cm, and wherein the soil sample is collected at a sampling amount of 50 g to 100 g.

* * * * *